United States Patent
Kiani

(10) Patent No.: US 9,211,072 B2
(45) Date of Patent: Dec. 15, 2015

(54) DISPOSABLE ACTIVE PULSE SENSOR

(71) Applicant: MASIMO CORPORATION, Irvine, CA (US)

(72) Inventor: Massi Joe E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 4 days.

(21) Appl. No.: 14/280,306

(22) Filed: May 16, 2014

(65) Prior Publication Data

US 2014/0343436 A1 Nov. 20, 2014

Related U.S. Application Data

(63) Continuation of application No. 12/147,299, filed on Jun. 26, 2008, now Pat. No. 8,764,671.

(60) Provisional application No. 60/946,979, filed on Jun. 28, 2007.

(51) Int. Cl.
| | |
|---|---|
| *A61B 5/02* | (2006.01) |
| *A61B 5/024* | (2006.01) |
| *A61B 5/00* | (2006.01) |
| *A61B 5/026* | (2006.01) |
| *A61B 5/1455* | (2006.01) |

(52) U.S. Cl.
CPC ........... *A61B 5/02427* (2013.01); *A61B 5/0048* (2013.01); *A61B 5/0051* (2013.01); *A61B 5/0261* (2013.01); *A61B 5/14551* (2013.01); *A61B 5/14552* (2013.01); *A61B 5/6826* (2013.01); *A61B 5/7221* (2013.01)

(58) Field of Classification Search
CPC ........................................................ A61B 5/021
USPC .......................................................... 600/500
See application file for complete search history.

(56) References Cited

U.S. PATENT DOCUMENTS

| | | | |
|---|---|---|---|
| 4,608,990 A * | 9/1986 | Elings | 600/317 |
| 4,960,128 A | 10/1990 | Gordon et al. | |
| 4,964,408 A | 10/1990 | Hink et al. | |
| 5,041,187 A | 8/1991 | Hink et al. | |
| 5,069,213 A | 12/1991 | Polczynski | |
| 5,163,438 A | 11/1992 | Gordon et al. | |
| 5,319,355 A | 6/1994 | Russek | |
| 5,337,744 A | 8/1994 | Branigan | |
| 5,341,805 A | 8/1994 | Stavridi et al. | |
| D353,195 S | 12/1994 | Savage et al. | |
| D353,196 S | 12/1994 | Savage et al. | |

(Continued)

*Primary Examiner* — Patricia Mallari
*Assistant Examiner* — Vasuda Ramachandran
(74) *Attorney, Agent, or Firm* — Knobbe, Martens, Olson & Bear LLP

(57) ABSTRACT

A disposable active pulse sensor has an emitter that generates optical radiation having a plurality of wavelengths, a detector that is responsive to the optical radiation and an unbalanced electrical motor that vibrates when energized. A tape assembly removably attaches the emitter, the detector and the unbalanced electrical motor to a tissue site. The tape assembly also physically mounts the emitter, the detector and the unbalanced electrical motor in a spatial arrangement so that vibration from the unbalanced electrical motor induces pulsatile blood flow within the tissue site, the emitter transmits the optical radiation into the tissue site and the detector generates a sensor signal responsive to the intensity of the optical radiation after attenuation by the pulsatile blood flow within the tissue site.

23 Claims, 5 Drawing Sheets

(56) References Cited

U.S. PATENT DOCUMENTS

| | | | |
|---|---|---|---|
| 5,377,676 A | 1/1995 | Vari et al. | |
| D359,546 S | 6/1995 | Savage et al. | |
| 5,431,170 A | 7/1995 | Mathews | |
| D361,840 S | 8/1995 | Savage et al. | |
| 5,441,512 A * | 8/1995 | Muller | 606/169 |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,562,002 A | 10/1996 | Lalin | |
| 5,590,649 A | 1/1997 | Caro et al. | |
| 5,602,924 A | 2/1997 | Durand et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A * | 1/1999 | Kiani-Azarbayjany et al. | 600/322 |
| 5,890,929 A | 4/1999 | Mills et al. | |
| 5,904,654 A * | 5/1999 | Wohltmann et al. | 600/481 |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,045,509 A | 4/2000 | Caro et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,285,896 B1 | 9/2001 | Tobler et al. | |
| 6,301,493 B1 | 10/2001 | Marro et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,430,437 B1 | 8/2002 | Marro | |
| 6,430,525 B1 | 8/2002 | Weber et al. | |
| 6,463,311 B1 | 10/2002 | Diab | |
| 6,470,199 B1 | 10/2002 | Kopotic et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,541,756 B2 | 4/2003 | Schulz et al. | |
| 6,542,764 B1 | 4/2003 | Al-Ali et al. | |
| 6,580,086 B1 | 6/2003 | Schulz et al. | |
| 6,584,336 B1 | 6/2003 | Ali et al. | |
| 6,595,316 B2 | 7/2003 | Cybulski et al. | |
| 6,597,932 B2 | 7/2003 | Tian et al. | |
| 6,597,933 B2 | 7/2003 | Kiani et al. | |
| 6,606,511 B1 | 8/2003 | Ali et al. | |
| 6,632,181 B2 | 10/2003 | Flaherty et al. | |
| 6,639,668 B1 | 10/2003 | Trepagnier | |
| 6,640,116 B2 | 10/2003 | Diab | |
| 6,643,530 B2 | 11/2003 | Diab et al. | |
| 6,650,917 B2 | 11/2003 | Diab et al. | |
| 6,654,624 B2 | 11/2003 | Diab et al. | |
| 6,658,276 B2 | 12/2003 | Pishney et al. | |
| 6,661,161 B1 | 12/2003 | Lanzo et al. | |
| 6,671,531 B2 | 12/2003 | Al-Ali et al. | |
| 6,678,543 B2 | 1/2004 | Diab et al. | |
| 6,684,090 B2 | 1/2004 | Ali et al. | |
| 6,684,091 B2 | 1/2004 | Parker | |
| 6,697,656 B1 | 2/2004 | Al-Ali | |
| 6,697,657 B1 | 2/2004 | Shehada et al. | |
| 6,697,658 B2 | 2/2004 | Al-Ali | |
| RE38,476 E | 3/2004 | Diab et al. | |
| 6,699,194 B1 | 3/2004 | Diab et al. | |
| 6,714,804 B2 | 3/2004 | Al-Ali et al. | |
| RE38,492 E | 4/2004 | Diab et al. | |
| 6,721,582 B2 | 4/2004 | Trepagnier et al. | |
| 6,721,585 B1 | 4/2004 | Parker | |
| 6,725,075 B2 | 4/2004 | Al-Ali | |
| 6,728,560 B2 | 4/2004 | Kollias et al. | |
| 6,735,459 B2 | 5/2004 | Parker | |
| 6,745,060 B2 | 6/2004 | Diab et al. | |
| 6,760,607 B2 | 7/2004 | Al-All | |
| 6,770,028 B1 | 8/2004 | Ali et al. | |
| 6,771,994 B2 | 8/2004 | Kiani et al. | |
| 6,792,300 B1 | 9/2004 | Diab et al. | |
| 6,813,511 B2 | 11/2004 | Diab et al. | |
| 6,816,741 B2 | 11/2004 | Diab | |
| 6,822,564 B2 | 11/2004 | Al-Ali | |
| 6,826,419 B2 | 11/2004 | Diab et al. | |
| 6,830,711 B2 | 12/2004 | Mills et al. | |
| 6,850,787 B2 | 2/2005 | Weber et al. | |
| 6,850,788 B2 | 2/2005 | Al-Ali | |
| 6,852,083 B2 | 2/2005 | Caro et al. | |
| 6,861,639 B2 | 3/2005 | Al-Ali | |
| 6,898,452 B2 | 5/2005 | Al-Ali et al. | |
| 6,920,345 B2 | 7/2005 | Al-Ali et al. | |
| 6,931,268 B1 | 8/2005 | Kiani-Azarbayjany et al. | |
| 6,934,570 B2 | 8/2005 | Kiani et al. | |
| 6,939,305 B2 | 9/2005 | Flaherty et al. | |
| 6,943,348 B1 | 9/2005 | Coffin IV | |
| 6,950,687 B2 | 9/2005 | Al-Ali | |
| 6,961,598 B2 | 11/2005 | Diab | |
| 6,970,792 B1 | 11/2005 | Diab | |
| 6,979,812 B2 | 12/2005 | Al-Ali | |
| 6,985,764 B2 | 1/2006 | Mason et al. | |

(56) References Cited

U.S. PATENT DOCUMENTS

| | | |
|---|---|---|
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty et al. |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,224,411 B2 | 7/2012 | Al-Ali et al. |
| 8,228,181 B2 | 7/2012 | Al-Ali |
| 8,229,533 B2 | 7/2012 | Diab et al. |

(56) References Cited

U.S. PATENT DOCUMENTS

| | | |
|---|---|---|
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | Mchale et al. |
| 8,274,360 B2 | 9/2012 | Sampath et al. |
| 8,301,217 B2 | 10/2012 | Al-Ali et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | Macneish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| 8,690,799 B2 | 4/2014 | Telfort et al. |
| 2003/0220576 A1* | 11/2003 | Diab .................. 600/502 |
| 2005/0197550 A1* | 9/2005 | Al-Ali et al. .......... 600/323 |
| 2006/0079479 A1 | 4/2006 | Biaggioni |
| 2006/0211932 A1 | 9/2006 | Al-Ali et al. |

\* cited by examiner

DISPOSABLE ACTIVE PULSE SENSOR

REFERENCE TO RELATED APPLICATION

The present application is a continuation of U.S. patent application Ser. No. 12/147,299, filed Jun. 26, 2008, titled "Disposable Active Pulse Sensor," which application claims priority benefit under 35 U.S.C. §119(e) from U.S. Provisional Application No. 60/946,979, filed Jun. 28, 2007, entitled "Disposable Active Pulse Sensor." All of the above-referenced application are hereby incorporated by reference herein in their entireties.

BACKGROUND OF THE INVENTION

Pulse oximetry is widely accepted noninvasive procedure for measuring the oxygen saturation level of arterial blood, an indicator of a person's oxygen supply. A typical pulse oximetry system utilizes a sensor applied to a patient tissue site. The sensor has emitters that transmit optical radiation of at least red and infrared (IR) wavelengths into the tissue site. A detector responds to the intensity of the optical radiation after attenuation by pulsatile arterial blood flowing within the tissue site. Based on this response, a processor determines measurements for oxygen saturation and pulse rate. In addition, a pulse oximeter may display a plethysmograph waveform, which is visualization of blood volume change within the illuminated tissue caused by the pulsatile arterial blood flow over time.

SUMMARY OF THE INVENTION

Pulse oximeters capable of reading through motion induced noise are available from Masimo Corporation ("Masimo") of Irvine, Calif. Moreover, portable and other pulse oximeters capable of reading through motion induced noise are disclosed in at least U.S. Pat. Nos. 6,770,028, 6,658, 276, 6,157,850, 6,002,952 5,769,785, and 5,758,644, which are assigned to Masimo and are incorporated by reference herein. Corresponding low noise sensors are also available from Masimo and are disclosed in at least U.S. Pat. Nos. 6,985,764, 6,813,511, 6,792,300, 6,256,523, 6,088,607, 5,782,757 and 5,638,818, which are assigned to Masimo and are incorporated by reference herein. Such reading through motion pulse oximeters and low noise sensors have gained rapid acceptance in a wide variety of medical applications, including surgical wards, intensive care and neonatal units, general wards, home care, physical training, and virtually all types of monitoring scenarios.

Further, noninvasive blood parameter monitors capable of measuring blood parameters in addition to Sp02, such as HbCO, HbMet and total hemoglobin (Hbt) and corresponding multiple wavelength optical sensors are also available from Masimo. Noninvasive blood parameter monitors and corresponding multiple wavelength optical sensors are described in at least U.S. patent application Ser. No. 11/367, 013, filed Mar. 1, 2006 and entitled Multiple Wavelength Sensor Emitters and U.S. patent application Ser. No. 11/366, 208, filed Mar. 1, 2006 and entitled Noninvasive Multi-Parameter Patient Monitor, both assigned to Masimo Laboratories, Irvine, Calif. (Masimo Labs) and both incorporated by reference herein.

Problems arise with pulse oximetry and other blood parameter monitoring systems when a tissue site has low blood perfusion and a corresponding weak sensor signal leading to invalid physiological measurements. To strengthen the sensor signal in low perfusion situations, an active pulse sensor actively induces a pulse in a controlled manner. That is, a sensor signal is generated according to a mechanically-induced active pulse rather than a heart-induced arterial pulse. Active pulse monitoring is described in U.S. Pat. No. 6,931, 268 entitled Active Pulse Blood Constituent Monitoring, which is assigned to Masimo and incorporated by reference herein.

One aspect of a disposable active pulse sensor is an emitter that generates optical radiation having a plurality of wavelengths, a detector that is responsive to the optical radiation and an unbalanced electrical motor that vibrates when energized. A tape assembly removably attaches the emitter, the detector and the unbalanced electrical motor to a tissue site. The tape assembly also physically mounts the emitter, the detector and the unbalanced electrical motor in a spatial arrangement so that vibration from the unbalanced electrical motor induces pulsatile blood flow within the tissue site, the emitter transmits the optical radiation into the tissue site and the detector generates a sensor signal responsive to the intensity of the optical radiation after attenuation by the pulsatile blood flow within the tissue site.

Another aspect of a disposable active pulse sensor is a method for inducing pulsatile blood flow within a tissue site so as to determine at least one constituent of the pulsatile blood flow. An emitter, a detector and an unbalanced electric motor are removably attached to a tissue site. The tissue site is illuminated with optical radiation having a plurality of wavelengths from the emitter. A sensor signal is generated from the detector responsive to the optical radiation after attenuation by pulsatile blood flow within the tissue site. If there is insufficient arterial pulsatile blood flow to measure a desired constituent of the pulsatile blood flow in response to the sensor signal, the unbalanced electric motor is energized so as to induce a sufficient pulsatile blood flow within the tissue site from motor vibrations.

A further aspect of a disposable active pulse sensor is an emitter means for transmitting optical radiation having a plurality of wavelengths into a tissue site and a detector means for generating a sensor signal responsive to the optical radiation after attenuation by pulsatile blood flow within the tissue site. An active pulse means induces pulsatile blood flow within the tissue site of sufficient volume so as to allow the measurement of a plurality of blood constituents within the pulsatile blood flow. A tape means mounts the emitter means, detector means and active pulse means in a predetermined configuration and removably attaching the emitter means, detector means and active pulse means to the tissue site.

DETAILED DESCRIPTION OF THE PREFERRED EMBODIMENT

Figure 1:
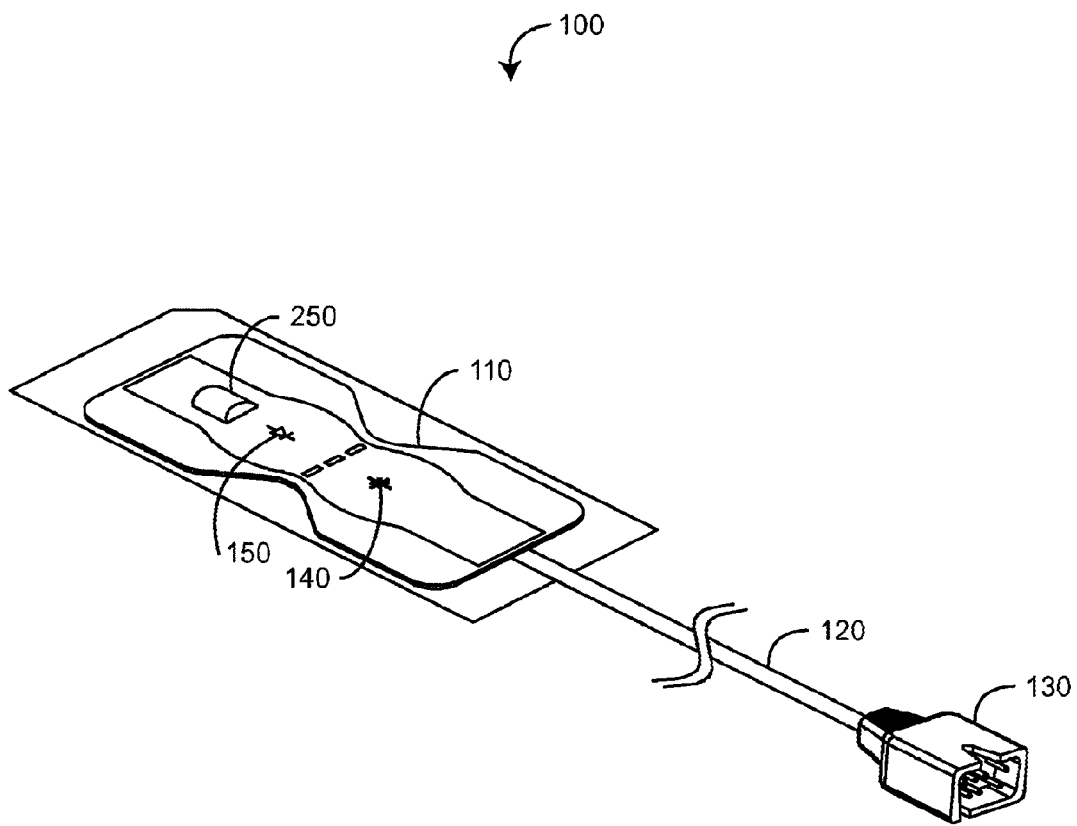
FIG. 1 is a perspective view of a disposable active pulse sensor.

FIG. 1 illustrates a disposable active pulse sensor 100 having a body 110, a cable 120 and a connector 130. In an embodiment, the body 110 is configured to wrap around a fingertip. The body incorporates an emitter 210 (FIG. 2) and a detector 220 (FIG. 2) that generates a sensor signal responsive to blood oxygen saturation, as described above. Advantageously, the body 110 also incorporates an active pulse element, such as an unbalanced electric motor 300 (FIG. 3) adapted to induce pulsatile blood flow in a tissue site so as to provide a sufficiently strong sensor signal for meaningful physiological measurements.

Figure 2:
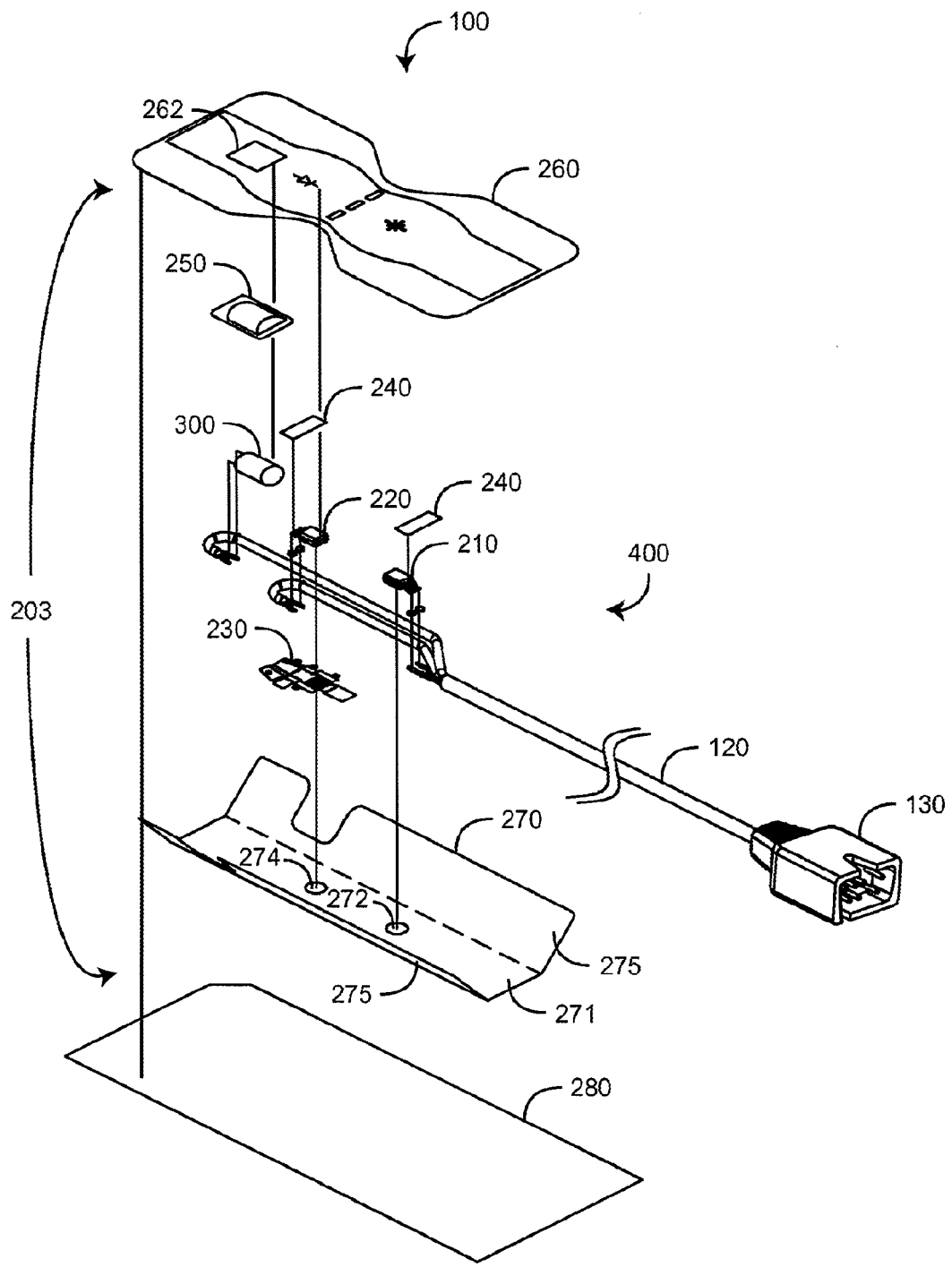
FIG. 2 is an exploded perspective view of a disposable active pulse sensor.

As shown in FIG. 1, an emitter marking 140 may designate the location of the emitter 210 (FIG. 2) within the body 110 allowing easy placement of the emitter 210 (FIG. 2) over a fingernail, for example, so as to transmit optical radiation into the blood perfused fingernail bed tissue underneath. Likewise, a detector marking 150 may designate the location of the detector 220 (FIG. 2) within the body 110 allowing easy placement of the detector 220 (FIG. 2) on the fingertip opposite the fingernail and the emitter 210 (FIG. 2). A housing 250 described in further detail below covers an unbalanced electric motor, which is located so as to mechanically vibrate the fingertip proximate the detector at a predetermined frequency so as to induce pulsatile blood flow at that frequency.

In the illustrated embodiment, the electric motor is located behind the detector 220 (FIG. 2), i.e. such that the detector is between the electric motor and the end of the finger tip. The electric motor may also be placed at other locations relative to the detector 220 (FIG. 2). In an embodiment, the electric motor is located in front of the detector 220 (FIG. 2), i.e. such that the motor is between the detector and the end of the fingertip. In an embodiment, the electric motor is located on or near the very end of the fingertip. In an embodiment, the electric motor is located on either side of the detector 220 (FIG. 2) along the fingertip.

In the illustrated embodiment, the electric motor is located immediately behind the detector 220 (FIG. 2), sharing the fingertip with the detector. In other embodiments, the electric motor is located at any of various other distances from the detector, such as between the first and second finger joints for example. In yet other embodiments, the electric motor is placed at any of various distances behind the emitter along the top of the finger.

Also shown in FIG. 1, the cable 120 provides electrical communication between the emitter 210 (FIG. 2), the detector 220 (FIG. 2), the motor 300 (FIG. 3) and the connector 130. The connector 130 is adapted to electrically and mechanically connect the sensor 100 to a monitor 500 (FIG. 5) either directly or via a patient cable. The monitor 500 (FIG. 5) drives the emitters 210 (FIG. 2), receives the detector signal, provides physiological measurements and controls the electric motor 300 (FIG. 3), as described in further detail with respect to FIG. 5, below.

FIG. 2 further illustrates a disposable active pulse sensor 100 having a cable assembly 400, a motor housing 250 and a tape assembly 203. The cable assembly 400 has an emitter 210, a detector 220 and an unbalanced electric motor 300, which are interconnected to the cable 120 opposite the monitor connector 130. The emitter 210 is configured with at least red and infrared LEDs that, for finger attachment, project light through the fingernail and into the blood vessels and capillaries underneath. The detector 220 is positioned at the fingertip opposite the fingernail so as to detect the LED emitted light as it emerges from the finger tissues. In an embodiment, the unbalanced motor 300 is also positioned at the fingertip opposite the fingernail and configured to vibrate the fingertip while the motor 300 is activated so as to induce blood flow in the finger tissues. The motor housing 250 accommodates the motor 300 and facilitates securing the motor 300 within the tape assembly 203. An electromagnetic interference (EMI) shield 230 is attached to the detector 220 so as to reduce detector noise. Electrically insulating tapes 240 are attached to the emitter 210 and the shielded detector 220. The cable assembly 400 is terminated at the monitor connector 130. A monitor 500 (FIG. 5) activates the emitter 210 and motor 300 and receives a corresponding sensor signal from the detector 220 all via the monitor connector 130, as described in detail with respect to FIG. 5.

As shown in FIG. 2, the tape assembly 203 is adapted to attach the emitter 210, the detector 220 and the electric motor 300 to a tissue site, such as a fingertip. The tape assembly 203 has a face tape 260, a trifold wrap 270 and a release liner 280. The trifold wrap 270 has a center portion 271 disposed between foldable side portions 275, which are symmetrical about the center portion 271. The center portion 271 is attached to the emitter 210, the detector 220 and the electric motor 300 with an emitter aperture 272 aligned so as to pass light from the emitter 210 and a detector aperture 274 aligned so as to pass light to the detector 220. The trifold wrap 270 has a pressure sensitive adhesive (PSA) on the component side and a patient adhesive, such as Med 3044, on the center portion 271 of the patient side. The release liner 280 is removably attached to the patient side of the trifold wrap 270. The face tape 260 has a housing aperture 262 allowing the motor housing 250 to protrude through the aperture 262. The face tape 260 is fixedly attached to the trifold wrap 270 and removably attached to the release liner 280. In one embodiment, the trifold wrap 270 is polypropylene and the face tape 260 is a laminate.

In other embodiments, not shown, a disposable active pulse sensor utilizes a flexible circuit for physical and electrical attachment and interconnection of the emitter, detector and unbalanced electric motor components. The flexible circuit may have an integrated connector for attachment to a sensor cable or patient cable, which communicates with a monitor or the flexible circuit may be soldered to or otherwise permanently attached to an integrated sensor cable. Further, in other embodiments, the tape assembly may be layered without a tri-fold wrap, or the sensor assembly may have a tissue attachment mechanism in lieu of or in addition to adhesive tape.

In other embodiments, the disposable active pulse sensor may include multiple emitters, multiple detectors or multiple unbalanced motors or combinations of such multiple components. The emitter(s) may incorporate light sources other than or in addition to LEOs, such as laser diodes or fiber optics transmitting light from an external source. The LEOs or other light sources may emit light having multiple wavelengths in addition to or instead of pulse oximetry-related red and infrared wavelengths. For example, multiple wavelengths emitters may be utilized with a disposable active pulse sensor for the detection of blood constituents other than oxyhemoglobin and reduced hemoglobin and for the measurement of blood parameters other than oxygen saturation, such as carboxyhemoglobin (HbCO), methemoglobin (HbMet) and other abnormal hemoglobin constituents. Other blood parameters that may be measured to provide important clinical information are fractional oxygen saturation, total hemaglobin (Hbt), bilirubin and blood glucose, to name a few.

In other embodiments, a disposable active pulse sensor is configured as a reflectance or transflectance sensor. Other embodiments may be configured to attach to other tissue sites rather than a fingertip, such as ear, nose, forehead, foot, cheek and lip sites, to name a few. Further, other embodiments of a disposable active pulse sensor may have additional components to those described above, such as an information element (IE) as described in U.S. patent application Ser. No. 11/367,036, filed Mar. 1, 2006 and entitled Configurable Physiological Measurement System, or a sensor life indicator (SLI), as described in U.S. Pat. No. 7,186,966 entitled Amount of use Tracking Device and Method for Medical Product, both incorporated by reference herein.

Figure 3:
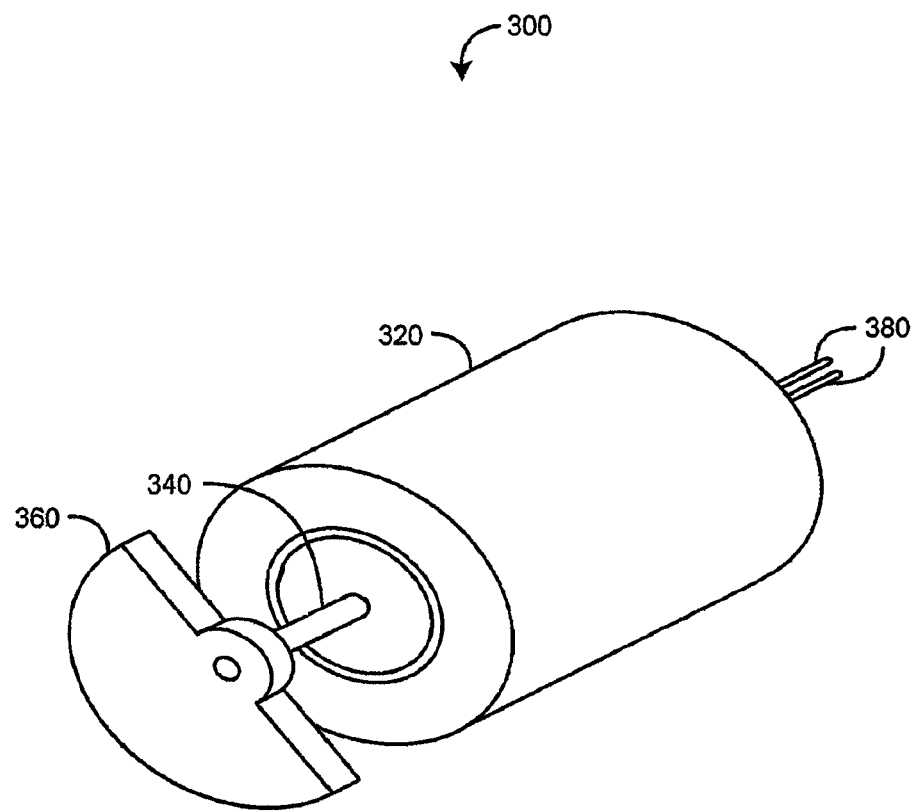
FIG. 3 is a perspective view of an unbalanced electric motor for inducing an active pulse in a tissue site.

FIG. 3 illustrates an unbalanced electric motor 300 having a motor body 320, a rotary shaft 340 and an unbalanced flywheel 360. The motor body 320 is generally cylindrical and accommodates the shaft 340, which extends along a center axis of the body 320. Electrical leads 380 extend from the body 320 opposite the shaft 340 so as to electrically connect the motor 300 to the cable 120 (FIG. 1). When the motor 300 is activated by a monitor 500 (FIG. 5) via the cable 120 (FIG. 1), the shaft 340 rotates the flywheel 360. In an embodiment, the flywheel 360 is a generally semi-circular disc centrally mounted to the shaft 340. When the shaft 340 rotates, the flywheel's eccentric imbalance causes the motor as a whole to vibrate at a predetermined frequency according to the motor rotational speed. This vibration "pulses" a tissue site, which creates a pulsatile blood flow. In other embodiments, the unbalanced motor 300 is configured with rotational elements other than the semi-circular flywheel, such as a circular flywheel composed of two or more materials of differing weights or densities, or an otherwise unsymmetrical flywheel. In other embodiments, the unbalanced motor is replaced with an alternative, electrically-activated vibrating component such as a piezo-electric element.

Figure 4:
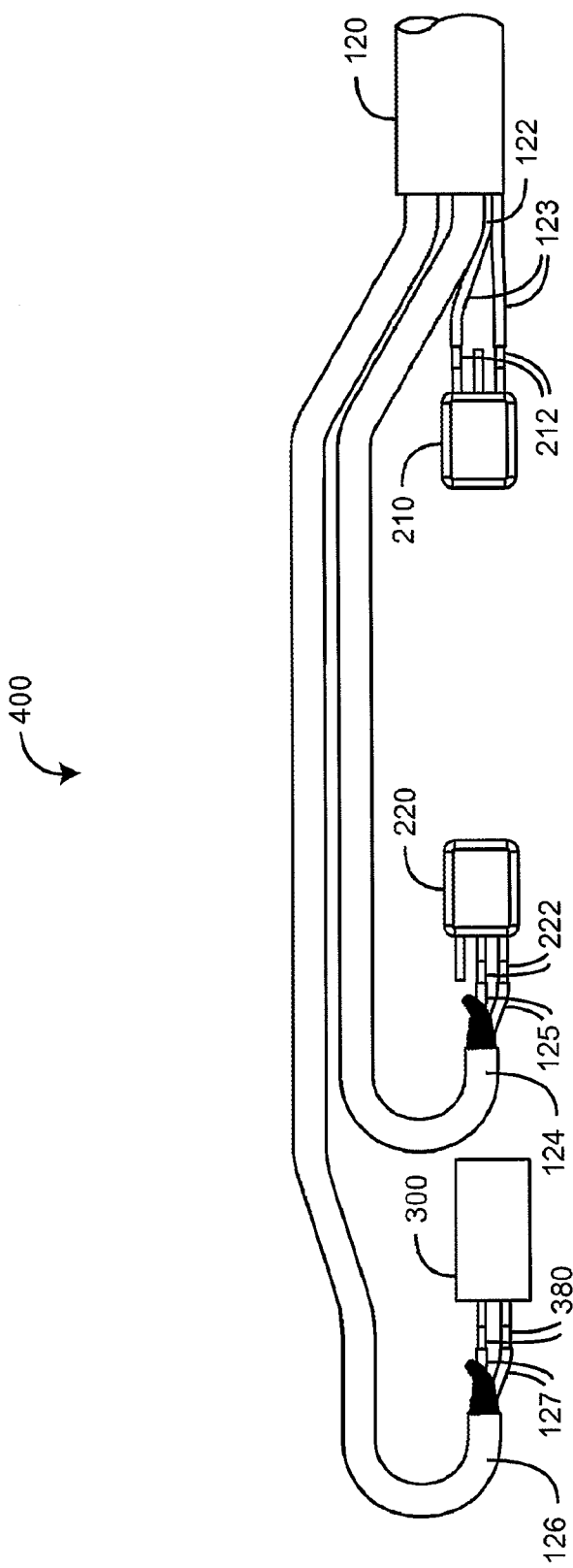
FIG. 4 is an untaped top view of a disposable active pulse sensor assembly.

FIG. 4 illustrates a cable assembly 400 having an emitter 210, a detector 220, an unbalanced electric motor 300 and a cable 120. The cable 120 has an emitter portion 122, a detector portion 124 and a motor portion 126. A pair of emitter wires 123 extend from the emitter portion 122 and are soldered to corresponding emitter leads 212. A pair of detector wires 125 extend from the detector portion 124 and are soldered to corresponding detector leads 222. A pair of motor wires 127 extend from the motor portion 126 and are soldered to corresponding motor leads 380. The cable wires 123, 125, 127 terminate at the monitor connector 130 (FIG. 2).

Figure 5:
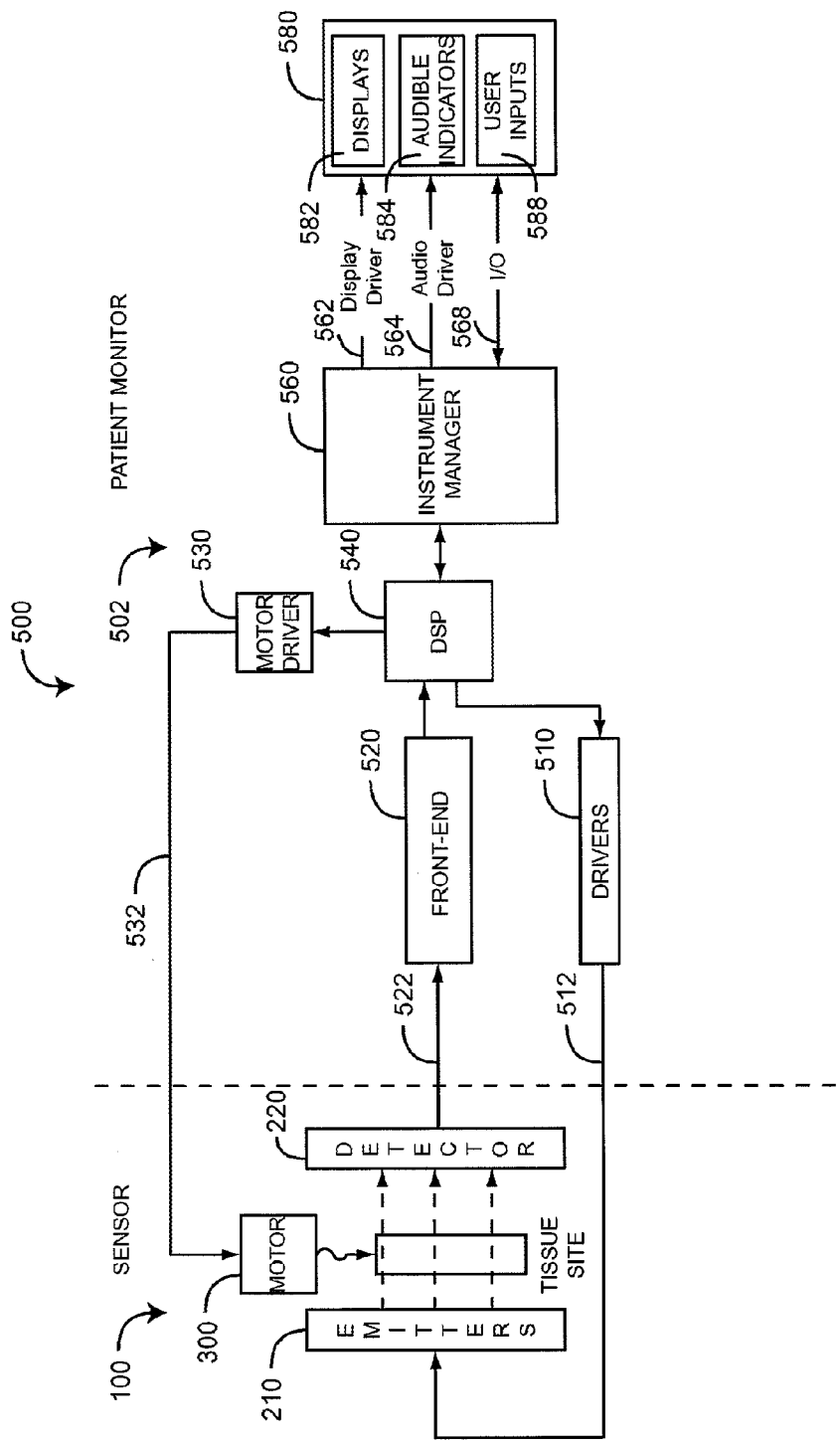
FIG. 5 is a general block diagram of a patient monitoring system including an active pulse sensor.

FIG. 5 illustrates a patient monitoring system 500 that generates one or more blood parameter measurements, such as Sp02, perfusion index (PI), HbCO, HbMet, and Hbt, to name a few. The patient monitoring system 500 is adapted to trigger an active pulse sensor as needed. In one embodiment, an active pulse is advantageously triggered when the monitor measures poor perfusion at the tissue site. In a particular embodiment, the active pulse is activated by a PI measurement below a predetermined threshold and deactivated between successful measurements. In an embodiment, an active pulse is triggered upon any measure indicating poor signal strength or signal quality. Signal quality and data confidence measures are described in U.S. Pat. No. 6,996,427 entitled Pulse Oximetry Data Confidence Indicator, assigned to Masimo and incorporated by reference herein. In an embodiment, an active pulse is triggered to induce a venous blood pulse so as to measure venous oxygen saturation or related venous blood parameters.

Also shown in FIG. 5, the patient monitor 502 communicates with the sensor 100 to receive one or more intensity signals indicative of one or more physiological parameters. Drivers 510 convert digital control signals into analog drive signals 512 capable of driving the emitter 210. A front-end 520 converts composite analog intensity signal(s) 522 from the detector(s) 220 into digital data input to the DSP 540. The DSP 540 comprises any of a wide variety of data and signal processors capable of executing programs for determining physiological parameters from input data. The DSP 540 generates an activation signal 532 from a motor driver 530 to the electric motor 300 when an active pulse is needed or desired.

In an embodiment, the patient monitoring system 500 controls the active pulse so as to accentuate a natural, heart-induced pulse. In particular, the patient monitor 502 generates an activation signal 532 so that an active pulse frequency and phase matches the frequency and phase of the natural pulse. In an embodiment, the DSP 540 executes a phase-locked-loop algorithm that has as inputs the natural pulse and the induced active pulse as derived from the detector signal 522 and an output that controls the activation signal 532 accordingly.

The instrument manager 560 may comprise one or more microcontrollers providing system management, such as monitoring the activity of the DSP 540. The instrument manager 560 also has an input/output (I/O) port 568 that provides a user and/or device interface for communicating with the monitor 502. In an embodiment, the I/O port 568 provides threshold settings via a user keypad, network, computer or similar device, as described below.

Further shown in FIG. 5 are one or more user I/O devices 580 including displays 582, audible indicators 584 and user inputs 588. The displays 582 are capable of displaying indicia representative of calculated physiological parameters such as one or more of a pulse rate (PR), plethysmograph, perfusion index (PI), signal quality and values of blood constituents in body tissue, including for example, oxygen saturation (Sp02), carboxyhemoglobin (HbCO) and methemoglobin (HbMet). The monitor 502 may also be capable of storing or displaying historical or trending data related to one or more of the measured parameters or combinations of the measured parameters. The monitor 502 may also provide a trigger for the audible indictors 584, which operate beeps, tones and alarms, for example. Displays 582 include for example readouts, colored lights or graphics generated by LEDs, LCDs or CRTs to name a few. Audible indicators 584 include speakers or other audio transducers. User input devices 588 may include, for example, keypads, touch screens, pointing devices, voice recognition devices, or the like.

A disposable active pulse sensor has been disclosed in detail in connection with various embodiments. These embodiments are disclosed by way of examples only and are not to limit the scope of the claims that follow. One of ordinary skill in art will appreciate many variations and modifications.

What is claimed is:

1. An active pulse sensor in communication with a monitor, the active pulse sensor comprising:
   an emitter that generates optical radiation having a plurality of wavelengths and transmits the optical radiation into a tissue site;
   a detector that generates a sensor signal responsive to the intensity of the optical radiation after attenuation by the pulsatile blood flow within the tissue site;
   a motor that vibrates when energized in response to an activation signal; and
   a tape means that is configured to removably attach the emitter, the detector and the motor to the tissue site so that vibration from the motor induces pulsatile blood flow within the tissue site when energized,
   wherein the sensor signal is communicated to the monitor, and the monitor is configured to:
      determine a signal quality of the sensor signal indicative of pulsatile blood flow;
      provide, based on the determined signal quality, the activation signal to the motor so as to induce pulsatile blood flow;
      receive the sensor signal while the activation signal is provided to the motor; and determine a physiological measurement using the sensor signal received while the activation signal is provided to the motor.

2. The active pulse sensor of claim 1, wherein the signal quality of the sensor signal is further indicative of perfusion index.

3. The active pulse sensor of claim 1, wherein the motor is energized so as to induce pulsatile blood flow within the tissue site to increase the signal quality of the sensor signal toward a threshold.

4. The active pulse sensor of claim 1, wherein, in response to determining that the signal quality of the sensor signal indicative of pulsatile blood flow does not satisfy a threshold, the motor is activated.

5. The active pulse sensor of claim 4, wherein, in response to determining that the signal quality of the sensor signal indicative of pulsatile blood flow does satisfy the threshold, the motor is deactivated.

6. The active pulse sensor of claim 1, wherein the tape assembly comprises a face tape that is shaped so as to attach the emitter, the detector and the motor to a finger.

7. The active pulse sensor of claim 6, wherein the face tape comprises:
a first portion mounted proximate the emitter so as to place the emitter over a fingernail; and
a second portion mounted proximate the detector and the motor so as to place the detector and the motor against a fingertip opposite the fingernail.

8. The active pulse sensor of claim 7 further comprising a housing mounted to the tape assembly so as to accommodate the motor within the housing.

9. The active pulse sensor of claim 8, wherein the motor comprises:
a generally cylindrical body having a first face, a second face and a central axis;
a shaft rotatably mounted along the axis and protruding from the first face;
an electrical connector accessible from the second face;
an unbalanced flywheel mounted on the protruding portion of the shaft; and
a DC power source in communications with the electrical connector so as to rotate the shaft at a frequency responsive to the electrical power applied to the electrical connector,
wherein the applied electrical power corresponds to a predetermined pulse rate induced in the tissue site by the motor.

10. A method of inducing pulsatile blood flow at a tissue site, the method comprising:
obtaining a first measurement signal from a physiological sensor configured to provide the first measurement signal in response to detection of optical radiation after attenuation of the optical radiation by a tissue site;
determining a signal quality of the first measurement signal;
in response to determining that the signal quality of the first measurement signal is low, initiating application of a vibrational force to the tissue site so as to induce pulsatile blood flow;
obtaining a second measurement signal from the physiological sensor during the application of the vibrational force; and
determining a physiological measurement using the second measurement signal.

11. The method of claim 10 further comprising:
determining a signal quality of the second measurement signal; and
in response to determining that the signal quality of the second measurement signal is high, deactivating the application of the vibrational force.

12. The method of claim 11, wherein the physiological sensor includes a motor configured to apply the vibrational force.

13. The method of claim 12, wherein the signal quality of the sensor signal is indicative of a degree of blood perfusion at the tissue site.

14. The method of claim 13, wherein a low signal quality is indicative of poor blood perfusion that is insufficient to measure a blood parameter.

15. The method of claim 13, wherein a high signal quality is indicative of blood perfusion sufficient to measure a blood parameter.

16. The method of claim 10, wherein the application of the vibrational force is initiated so as to induce pulsatile blood flow at the tissue site to increase the signal quality of the second measurement signal toward a threshold.

17. The method of claim 10 further comprising:
determining a desired induced pulse rate; and
transmitting DC power to a motor configured to apply the vibrational force at a level corresponding to the desired induced pulse rate.

18. The method of claim 17, wherein the motor is configured with a non-symmetrically weighted shaft so as to create vibration corresponding to rotations of the shaft.

19. An active pulse sensor in communication with a patient monitor, the active pulse sensor comprising:
a physiological parameter sensor means configured to sense at least pulsatile blood flow within a tissue site of a patient and generate a sensor signal;
an active pulse means configured to induce pulsatile blood flow when activated; and
a tape means that is configured to removably attach the physiological parameter sensor means and the active pulse means to the tissue site in a spatial arrangement so that the active pulse means induces pulsatile blood flow within the tissue site when activated,
wherein the sensor signal is communicated to the monitor, and the monitor is configured to:
determine a signal quality of the sensor signal indicative of pulsatile blood flow;
activate, based on the determined signal quality, the active pulse means so as to induce pulsatile blood flow; and
determine, based on the sensor signal communicated during activation of the active pulse means, a physiological measurement.

20. The active pulse sensor of claim 19, wherein the active pulse means comprises an unbalanced electrical motor means for vibrating the tissue site at a predetermined rate.

21. The active pulse sensor of claim 19, wherein the active pulse means is activated so as to induce pulsatile blood flow within the tissue site to increase the signal quality of the sensor signal toward a threshold.

22. The active pulse sensor of claim 19, wherein, in response to determining that the signal quality of the sensor signal indicative of pulsatile blood flow does not satisfy a threshold, the active pulse means is activated.

23. The active pulse sensor of claim 22, wherein, in response to determining that the signal quality of the sensor signal indicative of pulsatile blood flow does satisfy the threshold, the active pulse means is deactivated.

* * * * *